United States Patent
Duveneck et al.

[11] Patent Number: 5,959,292
[45] Date of Patent: *Sep. 28, 1999

[54] PROCESS FOR DETECTING EVANESCENTLY EXCITED LUMINESCENCE

[75] Inventors: Gert L. Duveneck, Bad Krozingen, Germany; Dieter Neuschäfer, Muttenz; Markus Ehrat, Magden, both of Switzerland

[73] Assignee: Novartis Corporation, Summit, N.J.

[*] Notice: This patent is subject to a terminal disclaimer.

[21] Appl. No.: 08/737,845
[22] PCT Filed: May 17, 1995
[86] PCT No.: PCT/EP95/01845
§ 371 Date: Nov. 25, 1996
§ 102(e) Date: Nov. 25, 1996
[87] PCT Pub. No.: WO95/33197
PCT Pub. Date: Dec. 7, 1995

[30] Foreign Application Priority Data

May 27, 1994 [CH] Switzerland ............... 1643/94

[51] Int. Cl.⁶ ..................... G02B 6/10
[52] U.S. Cl. ............. 250/227.11; 250/237 G; 385/12; 385/37; 385/130; 385/131
[58] Field of Search .......... 250/227.11, 237 G, 250/458.1, 459.1, 461.1, 461.2; 385/12, 13, 129, 130, 131, 147, 37; 356/128, 135, 136, 137; 422/82.05, 82.06, 82.07, 82.08, 82.09, 82.11; 436/518, 519, 527

[56] References Cited

U.S. PATENT DOCUMENTS

| | | | |
|---|---|---|---|
| 4,582,809 | 4/1986 | Black et al. | 436/527 |
| 4,815,843 | 3/1989 | Tiefenthaler et al. | 356/128 |
| 5,071,248 | 12/1991 | Tiefenthaler et al. | 356/128 |
| 5,081,012 | 1/1992 | Flanagan et al. | 435/7.9 |
| 5,082,629 | 1/1992 | Burgess, Jr. et al. | 422/82.11 |
| 5,120,131 | 6/1992 | Lukesz | 356/351 |
| 5,294,799 | 3/1994 | Aslund et al. | |
| 5,344,786 | 9/1994 | Attridge | 436/518 |
| 5,418,371 | 5/1995 | Aslund et al. | 250/458.1 |
| 5,822,472 | 10/1998 | Danielzik et al. | 385/12 |

FOREIGN PATENT DOCUMENTS

| | | |
|---|---|---|
| 0533074 | 3/1993 | European Pat. Off. . |
| 8607149 | 12/1986 | WIPO . |
| 8907756 | 8/1989 | WIPO . |
| 9006503 | 6/1990 | WIPO . |
| 9110122 | 7/1991 | WIPO . |
| 9113339 | 9/1991 | WIPO . |

OTHER PUBLICATIONS

Y. Zhou et al. Biosensors & Biodeceronics vol. 6, (1991) 595–607.

R.E. Kunz et al. SPIE vol. 2068/313–325 (1994).

*Primary Examiner*—Edward P. Westin
*Assistant Examiner*—John R Lee
*Attorney, Agent, or Firm*—Stephen G. Kalinchak; George R. Dohmann

[57] ABSTRACT

The invention relates to a process for detecting luminescence with a planar dielectric optical sensor platform consisting of a transparent substrate (a) to which a thin transparent waveguiding layer (b) is applied, which sensor platform is provided with a grating for the input-coupling of the excitation light and the refractive index of said substrate (a) is lower than the refractive index of the waveguiding layer (b), by bringing a liquid sample into contact with the layer (b), and measuring the luminescence produced by substances having luminescence properties in the sample, or by substances having luminescence properties immobilized on the layer (b), optoelectronically. The invention also relates to the use of the process in quantitative affinity sensing and to the use thereof for the quantitative determination of luminescent constituents in optically turbid solutions.

41 Claims, 2 Drawing Sheets

FIG. 1

PROCESS FOR DETECTING EVANESCENTLY EXCITED LUMINESCENCE

BACKGROUND OF INVENTION

The present invention relates to a process for detecting evanescently excited luminescence with a planar dielectric optical sensor platform based on a waveguide. The invention also relates to the use of said process in qualitative affinity sensing and to the use thereof for the selective quantitative determination of luminescent components in optically turbid solutions.

When a lightwave is coupled into a planar waveguide which is surrounded by optically thinner media it is conducted by total reflectance to the interfaces of the waveguiding layer. A planar waveguide consists in the simplest case of a 3-layer system: a substrate, a wave-conducting layer, and a superstrate (e.g. the sample for assaying), the wave-conducting layer having the highest refractive index. Additional interlayers can enhance the activity of the planar waveguide still further.

A fraction of the light energy penetrates the optically thinner media. This fraction is termed the evanescent (=fading) field. The strength of the evanescent field is very strongly dependent on the thickness of the waveguiding layer itself as well as on the ratio of the refractive indices of the waveguiding layer and of the surrounding media. In the case of thin waveguides, i.e. layer thicknesses of the same or lesser thickness than of the wavelength to be guided, it is possible to distinguish discrete modes of the conducted light. With an evanescent field it is possible, for example, to excite luminescence in optically thinner media, but only directly adjacent to the guided lightwave. This principle is called evanescent luminescence excitation.

Evanescent luminescence excitation is of great interest in the analytical field, as the excitation is limited to the direct environment of the waveguiding layer.

Methods and apparatus for detecting the evanescently excited luminescence of antibodies or antigens labelled with luminescent dyes are known and described, inter alia, in U.S. Pat. No. 4,582,809. The arrangement claimed therein uses an optical fibre for the evanescent luminescence excitation. Such optical fibres typically have a diameter of up to 1 millimeter and conduct a host of modes when laser light is coupled thereinto. The evanescently excited luminescence can be measured in simple manner only by the fraction tunnelled back into the fibre. The quite large dimensions of the apparatus and the fact that comparatively large sampling volumes are required are further drawbacks. The apparatus cannot be substantially reduced in size or even miniaturised to integrated optical sensors. An enhancement of the sensitivity is usually associated with an increase in the size of the apparatus.

Photometric instruments for detecting the luminescence of biosensors under the conditions of evanescent excitation with planar optical waveguides are likewise known and disclosed, inter alia, in WO 90/06503. The waveguiding layers used therein have a thickness of 160–1000 nm, and the coupling of light into the excitation wave is effected without coupling gratings.

Various attempts have been made to enhance the sensitivity of evanescently excited luminescence and to fabricate integrated optical sensors. Thus, for example, Biosensors & Bioelectronics 6 (1991), 595–607 reports on planar monomode or low-mode waveguides which are fabricated in a two-step ion exchange process and in which the coupling of light into the excitation wave is effected with prisms. The affinity system used is human immunoglobulin G/fluorescein-labelled protein A, wherein the antibody is immobilised on the waveguide and the fluorescein-labelled protein A to be detected, in phosphate buffer, is added to a film of polyvinyl alcohol with which the measuring region of the waveguide is covered. A substantial disadvantage of this process is that only minor differences in the refraction indices between waveguiding layer and substrate layer are achievable, resulting in a relatively low sensitivity.

The sensitivity is said to be 20 nm in fluorescein isothiocyanate bonded to protein A. This is still unsatisfactory for being able to detect microtraces, and a further enhancement of sensitivity is necessary. Moreover, the reproducibility and practical viability of coupling light into the excitation wave by prisms seems difficult on account of the considerable dependence of the coupling efficiency on the quality and size of the contact area between prism and waveguide.

Another principle is proposed in U.S. Pat. No. 5,081,012. The planar waveguiding layer has a thickness of 200 nm to 1000 nm and contains two grating structures, one of which is designed as a reflection grating, so that the lightwave coupled into the waveguide must traverse the sensor region between the grating structures at least twice. Enhanced sensitivity is said to be achieved by this means. One drawback is that the reflected radiation can lead to an unwanted increase of the background radiation intensity.

The fabrication of planar wave guides is a procedure in which the planar structure of the substrate, the constant thickness and homogeneity of the waveguiding layer and the refractive index of the material used therefore are very essential. This is described, inter alia, in EP-A-0 533 074, where the proposal is made to apply inorganic waveguides to plastic substrates. This procedure has the advantage that e.g. an economically useful structuring of the coupling grating can be carried out by etching the structure into the plastics material. On the other hand, however, high demands are made of the optical quality of the plastic substrates.

Planar waveguides afford considerable advantages in large-scale production over waveguides that are based on optical fibres. In particular, it is usually necessary to provide the chopped ends of the fibres with a final polish to obtain perfect optical quality. Planar waveguides, however, can be fabricated in large dimensions and afterwards punched out, broken or cut into the desired size. Providing the edges with a final finish can in most cases be dispensed with, thereby making large-scale production more economic.

Further advantages of planar waveguides with coupling gratings are the simple calibration in the measuring device or in the measuring set-up as well as the simple application of a coating, for example to immobilise an analyte. For this purpose it is possible to use standard methods of coating technology with which reproducible constant layer thicknesses can be prepared. Typical examples of such methods are spraying, knife-coating, spin-coating or dip-coating. The quality control can likewise be carried out by known and very exact methods. Suitable methods include microscopic or interferometric methods, ellipsometry or contact angle measurements. For the curved surfaces that occcur in waveguides based on optical fibres, these methods are inapplicable or applicable only with difficulty.

Besides the actual waveguiding layer, the nature of the coupling of the lightwave into the waveguiding layer constitutes a main problem. The requirements made of gratings for coupling light into tapered waveguides for integrated optical sensors are discussed, inter alia, in Chemical, Biochemical and Environmental Fiber Sensors V, Proc. SPIE, Vol 2068, 1–13, 1994. The depth modulation of the grating and the layer thickness of the waveguide are described in this reference as crucial features. The systems proposed therein can be typically used as integrated optical light pointers, but no reference is made to a luminescence to be detected.

If it is desired to use such planar waveguides with integrated coupling gratings for luminescence measurements, then the essential features for their usefulness and for achieving a high sensitivity are a sufficiently great input-coupling efficiency, as strong an evanescent field as possible, and a low attenuation of the guided wave. These features are crucially governed by the combination of refractive index of the waveguiding layer and of the substrate material and any interlayers present, the layer thickness of the waveguide, the structure, depth modulation and grating period of the coupling grating. In addition there is the requisite optical quality of the surfaces and their planar structure or roughness.

It has now been found that it is possible, in simple manner and without an additional reflection grating, to carry out a process for the evanescent excitation and detection of luminescence with high sensitivity by combining the aforementioned crucial features such as refractive index, layer thickness and depth modulation. Typically, the attenuation of the guided lightwave is then less than 3 dB/cm, thereby resulting in a long distance of the guided beam and a low scattering of the guided wave into the media surrounding it. In particular, it is preferred under these conditions to guide the TE0 and TM0 mode. The conduction distance suffices, in addition to measuring the luminescence, to be able to measure with great accuracy the absorption of the excitation light in the presence of an absorbing sample.

These planar waveguides, in which only one mode or a few modes are guided, are distinguished by a particularly high sensitivity and a miniaturised construction. Normally this sensitivity is not achieved by multimode waveguides of planar or fibrous construction or, if it is achieved, then this is only possible with substantially greater geometric dimensions.

The input-coupling efficiency of the coupling grating is high, so that the intensity of the lightwave coupled into the waveguide is likewise high, resulting in conjunction with the low attenuation in an already good sensitivity.

The sensitivity is further enhanced by the evanescent field being surprisingly strong and by the high electromagnetic field strengths thereby produced contributing to a further enhancement of sensitivity. The possibility is thereby afforded of detecting even minimal amounts of luminescent material at the surface of the waveguiding layer.

SUMMARY OF INVENTION

Accordingly, in one of its aspects the invention relates to a process for detecting luminescence with a planar dielectric optical sensor platform consisting of a transparent substrate (a) to which a thin transparent waveguiding layer (b) is applied, which sensor platform is provided with a grating for the input-coupling of the excitation light and the refractive index of said substrate (a) is lower than the refractive index of the waveguiding layer (b), by bringing a liquid sample into contact with the layer (b), and measuring the luminescence produced by substances having luminescence properties in the sample, or by substances having luminescence properties immobilised on the layer (b), optoelectronically, wherein (A) the excitation light is coupled into the planar waveguide and traverses the waveguiding layer, whereby the substances having luminescence properties are excited to luminescence in the evanescent field of the waveguiding layer, (B) the grating has a depth modulation of 3 to 60 nm, (C) the thickness of the layer (b) is 40 to 160 nm, and (D) the ratio of depth modulation to the thickness of the layer (b) is smaller than 0.5.

DETAILED DESCRIPTION OF INVENTION

Within the scope of this invention, a planar dielectric optical sensor platform means that said platform is in the form of a strip, a plate, a round disc or any other geometrical form, provided it can be seen by the naked eye to be planar. The chosen geometrical form is intrinsically not crucial and can be governed by the construction of the entire apparatus into which the sensor platform is built. It may, however, also be used as an independent element, spatially separated from the source of excitation light and from the optoelectronic detection system. Preferred arrangements are those that permit substantial miniaturisation.

A suitable substrate is typically any kind of glass or quartz. It is preferred to use a glass that has as low an optical refractive index as possible and as low an intrinsic luminescence as possible, and which can be optically treated in as simple a manner as possible, for example etching, cutting and polishing. The substrate must be transparent at least at the excitation and emission wavelength.

The substrate may also be a plastics material as described e.g. in EP-A-0 533 074.

The substrate may also be provided with a thin layer that has a refractive index lower than, or identical to, that of the substrate, and which has a thickness of, or less than 10 $\mu$m. This layer can serve to reduce the surface roughness of the substrate and may consist of a thermoplastic, thermosetting or structurally crosslinked plastic, or also of an inorganic material such as $SiO_2$.

Only essentially parallel light is suitable for luminescence excitation. Within the scope of this invention, the expression "essentially parallel" shall be understood as meaning a divergence of less than 5°. This means that light may be weakly divergent or weakly convergent.

It is preferred to use coherent light for the luminescence excitation, more particularly laser light of wavelength 300 to 1100 nm, more particularly still of 450 to 850 nm and, most preferably, of 480 to 700 nm.

Lasers which may suitably be used are dye lasers, gas lasers, solid lasers and semiconductor lasers. Where necessary, the emission wavelength can also be doubled by nonlinear crystal optics. The beam can also be still further focused by optical elements, polarised, or attenuated by grey filters. Particularly suitable lasers are argon-ion lasers and helium-neon lasers which emit at wavelengths between 457 nm and 514 nm and, respectively, between 543 nm and 633 nm. Very particularly suitable lasers are diode lasers or frequency-doubled diode lasers of semiconductor material that emit at a fundamental wavelength between 630 nm and 1100 nm, as they permit a substantial miniaturisation of the entire sensor system on account of their small dimensions and low power consumption.

Within the scope of this invention the term "sample" shall be taken to mean the entire solution to be assayed which may contain a substance to be detected—the analyte. The detection can be made in a single-step or multistep assay in the course of which the surface of the sensor platform is contacted with one or more solutions. At least one of the solutions employed can contain a substance having luminescence properties which can be detected in the practice of this invention.

If a substance having luminescence properties is already adsorbed on the waveguiding layer (b), then the sample may also be free from luminiscent components. The sample can contain further constituents, typically pH buffers, salts, acids, bases, surface-active substances, viscosity-influencing modifiers or dyes. In particular, a physiological saline solution can be used as solvent. If the luminescent constituent itself is liquid, then the addition of a solvent can be dispensed with. In this case the sample can contain up to 100% of component having luminescence properties.

The sample may further contain a biological medium, for example egg yolk, a body fluid or constituents thereof, in particular blood, serum, plasma or urine. Furthermore, the sample may consist of surface water, solutions of extracts of natural or synthetic media such as soil or parts of plants, bioprocess broths or synthesis broths.

The sample can either be undiluted or used additionally with a solvent.

Suitable solvents are water, aqueous buffer and protein solutions and organic solvents. Suitable organic solvents are alcohols, ketones, esters, and aliphatic hydrocarbons. It is preferred to use water, aqueous buffers or a mixture of water and a water-miscible organic solvent.

The sample can, however, also contain constituents that are insoluble in the solvent, for example pigment particles, dispersants, natural and synthetic oligomers or polymers. In this case the sample is in the form of an optically turbid dispersion or emulsion.

Suitable luminescent compounds are luminescent dyes having a luminescence in the wavelength range from 330 nm to 1000 nm, typically including rhodamines, fluorescein derivatives, coumarin derivatives, distyryl biphenyls, stilbene derivatives, phthalocyanines, naphthalocyanines, polypyridyl-ruthenium complexes such as tris(2,2'-bipyridyl)-ruthenium chloride, tris(1,10-phenanthroline) ruthenium chloride, tris(4,7-diphenyl-1,10-phenanthroline) ruthenium chloride and polypyridyl-phenazine-ruthenium complexes, platinum-porphyrin complexes such as octaethyl-platinum-porphyrin, long-life europium and terbium complexes or cyanine dyes. Particularly suitable for analyses in blood or serum are dyes having absorption and emission wavelengths in the range from 600–900 nm.

Particularly suitable luminescent compounds are dyes such as fluorescein derivatives which contain functional groups with which they can be covalently bonded, for example fluorescein isothiocyanate.

Also very suitable are the functional fluorescent dyes available from Biological Detection Systems Inc., for example the mono- and bifunctional Cy5.5™ dyes also described, inter alia, in Clinical Chemistry 40 (9): 1819–1822, 1994.

The preferred luminescence is fluorescence.

The luminescent dyes eligible for use may also be chemically bonded to polymers or to one of the binding partners in biochemical affinity systems, e.g. antibodies or antibody fragments, antigens, proteins, peptides, receptors or their ligands, hormones or hormone receptors, oligonucleotides, DNA strands and RNA strands, DNA or RNA analogs, binding proteins such as protein A and G, avidin or biotin, enzymes, enzyme cofactors or inhibitors, lectins or carbohydrates. The covalent luminescent labelling last mentioned is the preferred utility for reversible or irreversible (bio) chemical affinity assays. It is further possible to use luminescent-labelled steroids, lipids and chelators. Intercalating luminescent dyes are also of particular interest for hybridisation assays with DNA strands or oligonucleotides, especially if—like different ruthenium complexes—they exhibit enhanced luminescence in the intercalation. If these luminescent-labelled compounds are brought into contact with their affinity partners immobilised on the surface of the sensor platform, then the binding can be determined quantitatively from the measured intensity of luminescence. A quantitative determination of the analyte is also possible by measuring the change in luminescence when the sample interacts with the luminophores, for example in the form of luminescence quenching with oxygen or of luminescence enhancement by conformation modifications of proteins.

The refractive index of the waveguiding layer must be greater than that of the substrate and of any interlayers employed. Preferably the planar transparent waveguiding layer consists of a material having a refractive index greater than 2.

Suitable materials are typically inorganic materials, preferably inorganic metal oxides such as $TiO_2$, $ZnO$, $Nb_5O_5$, $Ta_2O_5$, $HfO_2$, or $ZrO_2$.

$Ta_2O_5$ and $TiO_2$ are preferred.

The thickness of the transparent waveguiding layer is preferably 80 to 160 nm.

The depth modulation of the grating for coupling the excitation light into the waveguiding layer is preferably 5 to 30 nm.

The grating preferably has a line to space ratio of 0.5–2. By line to space ratio is meant typically in a rectangular grating the ratio of the width of the lines to the width of the spaces.

The grating for coupling the excitation light has the configuration of an optical diffraction grating, preferably of a relief grating. The relief structure can be of different form. For example, sinusoidal, rectangular or saw-tooth structures are suitable. Methods of fabricating such gratings are known. Mainly photolithographic or holographic methods and etching techniques are used for making them, for example the methods described in Chemical, Biochemical and Environmental Fiber Sensors V. Proc. SPIE, Vol 2068, 1–13, 1994.

The grating structure can be produced on the substrate and afterwards transferred to the waveguiding layer in which the grating structure is then imaged, or the grating is produced in the waveguiding layer itself.

The grating period can be from 200 to 1000 nm, and the grating conveniently exhibits only one periodicity, i.e. is monodiffractive.

In the process of this invention the sample can be brought into contact with the waveguiding layer in the immobile state as well as guided continuously over it, and the cycle can be open or closed.

A specific embodiment of the process consists in immobilising the substances having luminescent properties used for detecting the analyte direct at the surface of the waveguiding layer (b). The substance having luminescent properties can be, for example, a luminophore which is bound to a protein and which can thereby be excited to luminescence in this manner at the surface of the waveguiding layer. If a partner having affinity for the protein is guided over this immobilised layer, then the luminescence can be modified and the amount of said partner can be determined in this manner. In particular, both partners of an affinity complex can also be labelled with luminophores so as to be able to effect the determination of concentrations from the energy transfer between the two, e.g., in the form of luminescence quenching.

Another preferred embodiment of the process for carrying out chemical or biochemical affinity assays consists in immobilising on the surface of the sensor platform a specific binding partner as chemical or biochemical detector substance for the analyte itself or for one of the binding partners. The assay can be a single-step or multistep assay in the course of which, in successive steps, one or more than one solution containing binding partners for the detector substances immobilised on the surface of the sensor platform is guided, the analyte becoming bound in one of the partial steps. The detection of the analyte is effected by binding luminescent-labelled participants in the affinity assay. The luminescent-labelled substances used may consist of one or more than one binding partner of the affinity assay, or also of an analog of the analyte provided with a luminophore. The sole criterion is that the presence of the analyte leads selectively to a luminescence signal or selectively to a change in the luminescence signal.

The immobilisation of the detector substances may typically be carried out by hydrophobic absorption or covalent bonding direct on the waveguide layer or after chemical modification of the surface, for example by silanisation or applying a polymer layer. In addition, a thin interlayer consisting e.g. of $SiO_2$ can be applied as adhesion-promoting layer direct to the waveguide layer to facilitate the immobilisation of the detector substances direct on the waveguide. The thickness of this interlayer should not exceed 50 nm, preferably 20 nm.

Suitable detector substances are typically antibodies for antigens, binding proteins such as protein A and G for immunoglobulins, receptors for ligands, oligonucleotides and single strands of RNA and DNA for their complementary strands, avidin for biotin, enzymes for enzyme substrates, enzyme cofactors or inhibitors, lectins for carbohydrates. Which of the respective affinity partners is immobilised on the surface of the sensor platform will depend on the architecture of the assay.

The assay itself can be a single-step complexing process, for example a competitive assay, or also a multistep process, for example a sandwich assay.

In the simplest case of the competitive assay, the sample which contains the analyte in unknown concentration as well as a known amount of a compound that is similar except for luminescent labelling is brought in to contact with the surface of the sensor platform, where the luminscent-labelled and unlabelled molecules compete for the binding sites at their immobilised detector substances. A maximum luminescence signal is achieved in this assay configuration when the sample contains no analyte. With increasing concentration of the substance to be detected, the luminescence signals under observation become lower.

In a competitive immunoassay it does not necessarily have to be the antibody which is immobilised: the antigen too can be immobilised on the surface of the sensor platform as detector substance. Usually it is immaterial which of the partners is immobilised in chemical or biochemical affinity assays. This is a basic advantage of luminescence-based assays over methods such as surface plasmon resonance or interferometry, which are based on the change in adsorbed mass in the evanescent field of the waveguiding layer.

Further, in the case of competitive assays the competition does not need to be limited to binding sites at the surface of the sensor platform. For example, a known amount of an antigen can also be immobilised on the surface of the sensor platform and then brought into contact with the sample which contains an unknown amount to be detected of the same antigen as analyte as well as luminescent-labelled antibodies. In this case the competition between antigens that are immobilised on the surface and present in solution takes place for binding of the antibodies.

The simplest case of a multistep assay is a sandwich immunoassay in which a primary antibody is immobilised on the surface of the sensor platform. The binding of the antigen to be detected and of the luminiscent-labelled secondary antibody used for carrying out the detection to a second epitope of the antigen can be effected either by successive contacting with the solution containing the antigen and a second solution containing the luminiscent-labelled antibody, or by combining these two solutions beforehand, so that, finally, the partial complex consisting of antigen and luminescent-labelled antibody is bound.

Affinity assays may also comprise further additional binding steps. For example, in the case of sandwich immunoassays protein A, which specifically binds immunoglobulins which then act as primary antibodies in a subsequent sandwich assay, which is carried out as described above, at their so-called $F_c$ part, can be immobilised on the surface of the sensor platform in a first step.

There is a whole host of further types of affinity assays, typically using the known avidin-biotin affinity system.

Examples of types of affinity assays will be found in J. H. Rittenburg, Fundamentals of Immunoassay; in Development and Application of Immunoassay for Food Analysis, J. H. Rittenburg (Ed.), Elsevier, Essex 1990, or in P. Tijssen, Practice and Theory of Enzyme Immunoassays, R. H. Burdon, P. H. van Knippenberg (Eds), Elsevier, Amsterdam 1985.

It is furthermore possible to use the surface of the sensor platform not only for single use but also to regenerate it Under suitable conditions, for example low pH, elevated temperature, using organic solvents or so-called chaotropic reagents (salts), it is possible to dissociate the affinity complexes seelctively without substantial impairment of the binding capacity of the immobilised detector substances. The exact conditions are strongly dependent on the particular affinity system.

Another essential embodiment of the process consists on the one hand in limiting the production of the signal—in the case of back-coupling this also applies to signal detection—to the evanescent field of the waveguide and, on the other, in the reversibility of the affinity complex formation as equilibrium process. Using suitable rates of flow in a continuous flow system it is possible to monitor in real time the binding or desorption or dissociation of bound luminescent-labelled affinity partners in the evanescent field. The process is therefore suitable for kinetic studies for determining different association or dissociation constants or also for displacement assays.

The detection of evanescently excited luminescence can be made by known methods. Photodiodes, photocells, photomultipliers, CCD cameras and detector arrays, for example CCD cells, may suitably be used. The luminescence can be imaged with optical elements such as mirrors, prisms, lenses, Fresnel lenses and gradient index lenses thereon. To select the emission wavelength it is possible to use known elements such as filters, prisms, monochromatic filters, dichromatic mirrors and diffraction gratings.

One embodiment of the process of this invention consists in detecting isotropically emitted, evanescently excited luminescence.

Another embodiment of the process of this invention comprises detecting at the edges of the sensor platform the evanescently excited luminescence coupled back into said sensor platform. This back-coupled fluorescence intensity is surprisingly high, so that a very good sensitivity can likewise be achieved by means of this procedure.

Another embodiment of the process of this invention consists in detecting the isotropically emitted, evanescently excited luminescence as well as the luminescence coupled back into the waveguide, independently of each other, but simultaneously. Because of the different selectivity of the two luminescence detection methods, which is dependent on the distance of the luminophores from the waveguide layer, additional information on the spatial distribution of the luminophores can be obtained in this embodiment. Hence this gives rise to the possibility of distinguishing between the photochemical fading of the luminophores and the dissociation of the affinity complexes carrying the luminophores.

One advantage of the process of this invention is that, besides the detection of luminescence, the absorption of the irradiated excitation light can also be determined. Compared with multimodal waveguides of optical fibre or planar construction, a substantially better signal-to-noise ratio is achieved in this case. The simultaneous measurement of luminescence and absorption makes it possible to determine luminescence quenching effects with high sensitivity.

The process can be carried out by irradiating with excitation light in continuous wave (cw) mode, i.e. excitation is effected with light intensity that is constant in time.

The process can, however, also be carried out by irradiation with excitation light in the form of a timed pulse with a pulse length of e.g. one picosecond up to 100 seconds, and by time-resolved detection of the luminescence—in the case of short pulse lengths—or at intervals of seconds to minutes. This method is particularly advantageous whenever it is desired e.g. to monitor the rate of a bond formation analytically or to prevent a decrease in the luminescence signal because of photochemical fading using short exposure times. By using appropriate short pulse length and suitable time-resolution of the detection it is further possible to distinguish scattered light, Raman emission and short-lived luminescence of any unwanted luminescent constituents of the sample and the sensor material from a luminescence of the labelling molecule, which is in this case preferably long-lived, by detecting the emission of the analyte only after this short-lived radiation has decayed. Moreover, time-resolved luminescence detection permits after pulsed excitation—just like modulated excitation and detection—investigation of the influence of the binding of the analyte on the decay of molecular luminescence. In addition to the specific recognition of the analyte by the immobilised detector substances and the spatial limitation of the signal production to the evanescent field of the waveguide, the molecular luminescence decay time can be utilised as a further criterion of selectivity.

The process can also be carried out by input-coupling the excitation light at one or more than one frequency with modulated intensity, and detecting the resultant phase shift and modulation of the sample luminescence.

The invention further relates to the use of the inventive process for the quantitative determination of analytes in chemical or biochemical affinity assays with known affinity partners and assay architectures by detecting the emission of labelled binding partners capable of luminescence, or by detecting changes in the luminescence properties of immobilised luminescent-labelled affinity partners by interaction with the analyte.

As signal production and detection are limited to the chemical or biochemical detection surface on the waveguide, and interference signals from the medium are discriminated, the binding of substances to the immobilised detector elements can be monitored in real time. It is therefore also possible to use the inventive process for affinity screening or for displacement assays, especially for pharmaceutical product development, by direct detection of association and dissociation rates in continuous flow systems with suitable flow rates.

In another of its aspects, the invention relates to the use of the inventive process for the quantitative determination of antibodies or antigens.

Yet another utility of the inventive process is for the quantitative determination of receptors or ligands, oligonucleotides, strands of DNA or RNA, DNA or RNA analogs, enzymes, enzyme substrates, enzyme cofactors or inhibitors, lectins and carbohydrates.

In a further aspect, the invention relates to the use of the inventive process for the selective quantitive determination of luminescent constituents in optically turbid fluids.

Optically turbid fluids may typically be biological fluids such as egg yolk, body fluids such as blood, serum or plasma, and also samples emanating from environmental analysis, including surface water, dissolved soil extracts and dissolved plant extracts. Suitable fluids are also the reaction solutions obtained in chemical production, in particular dye solutions or reaction solutions originating from the production of fluorescent whitening agents. Also suitable are all types of the dispersions and formulations typically used in the textile industry, provided these contain one or more than one luminescent component. The process can thus also be used for quality safeguarding.

Figure 1:
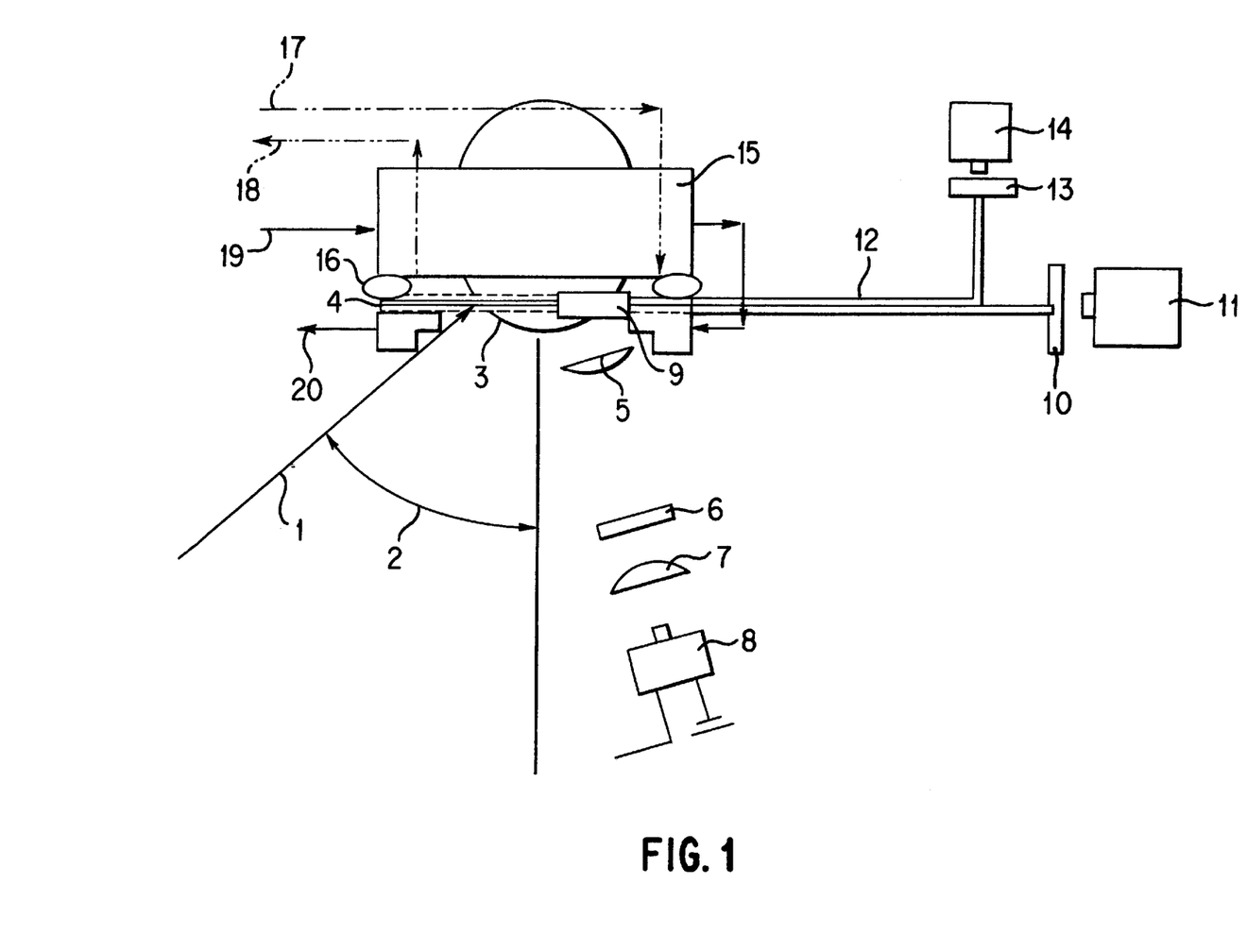
FIG. 1 shows schematically a cross-section of an arrangement of apparatus for carrying out the inventive process.
Figure 2A:
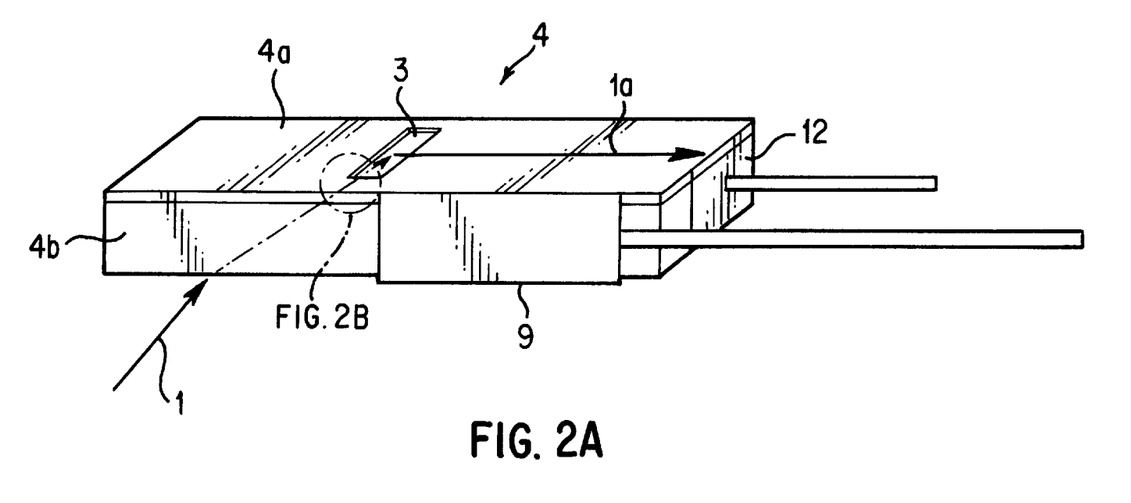
FIG. 2 shows schematically an enlarged section of the optical waveguide.
Figure 2B:
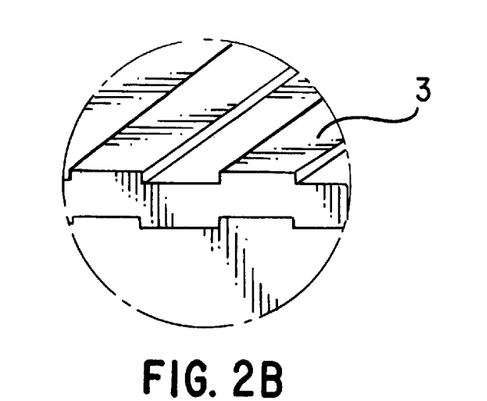

These embodiments of the invention are in detail:

Excitation optics and waveguide:

1 exciting laser beam,
1a guided mode
2 coupling angle
3 grating (depth 4–5 nm, period 750 nm, rectangular form)
4 optical sensor platform consisting of 4a and 4b
4a waveguiding layer ($Ta_2O_5$, n=2.317 at 488 nm),
4b substrate (Corning glass, n=1.538 at 488 nm).

Detection optics for the isotropically emitted luminescence 5 focusung lens of suitable focal length,
6 interference filter suitable for the maximum of luminescence with a half intensity width of e.g. 30 nm
7 focusing lens of suitable focal length,
8 detector (photodiode).

Detection optics for the luminescence coupled back into the sensor platform:

9 glass fibre bundle of rectangular cross-section
10 interference filter suitable for the maximum of luminescence with a half intensity width of e.g. 30 nm, 11 photodiode.

Detection of the transmitted light:

12 glass fibre bundle of rectangular cross-section,
13 interference filter suitable for the maximum of luminescence with a half intensity width of e.g. 30 nm,
14 photodiode.

Sample cell (rotatable):

15 upper part which—pressed against the sensor platform—together with this forms the flow cell,
16 sealing O ring,
17 entry port for fluid,
18 exit port for fluid,
19 entry port for thermostatic control,
20 exit port for thermostatic control.

The individual elements used for the arrangement are known and commercially available.

The following Examples illustrate the invention. The concentration M in all Examples denotes mol/l.

EXAMPLE 1

1.1 Optical Construction

The excitation light of an argon-ion laser (excitation wavelength 488 nm) is directed on to the grating of the waveguiding layer by means of a rotatable mirror from the back of the substrate. Sealed by O rings, a thermostatically-controlled flow cell is pressed from above against the face of the waveguiding layer. The cell has a volume of c. 0.07 ml. The luminescence of the sample excited in the evanescent field and the transmission of the excitation light are recorded simultaneously by 3 detectors in differing spatial arrangement. The arrangement is illustrated schematically in FIG. 1. Detector 8 consists of a photodiode (UDT UV-50, United Detector Technology, Hawthorne, Calif., USA), on to which the isotropically emitted luminescence is focused through interference filters and focusing lenses. Detector 14 consists of a photodiode (SR 1133, Hamamatsu) on to which the luminescence coupled back into the waveguide layer and observed under 90° for the direction of propagation of the continuous mode is guided by means of optical glass fibres and passed through an interference filter. The signal is enhanced by means of a transimpedence amplifier. The transmission light is guided in analogous manner by detector 11 in the direction of propagation of the mode, while passing through an interference filter, on to a photodiode (UDT UV-50, United Detector Technology, Hawthorne, Calif., USA), and enhanced.

1.2 Characterisation of the Sensor Materials and of the Coupling Result 1.2.1 Optical sensor platform geometry: 16 mm×48 mm×0.5 mm.

waveguiding layer: $Ta_2O_5$, n=2.317 at 488 nm, thickness 100±5 nm.

substrate: Corning glass C7059, n=1.538 at 488 nm.

Grating: rectangular grating with a depth modulation of 4–5 nm, grating period 750 nm.

1.2.2 Coupling result with excitation at 633 nm coupling angle: 4–5 (second refraction order)

coupling efficieny: 7% at grating site attenuation: 2,5 dB/cm.

1.3. Detection of Fluorescein-Labelled Immunoglobulin on Immobilised Protein A Sample solution:

1×10−8 M of fluorescein-labelled immunoglobulin (Sigma Chemicals, F-IgG);

0.5 l of phosphate buffer, consisting of 0.041 M of $Na_2HPO_4$ and 0.028 M of $KH_2PO_4$;

1 ml of POE-(20)-sorbitol monolaurate (Tween 20, ICI);

200 mg of sodium azide, 50 ml of methanol, bulked to 1 liter with distilled water.

The sensor is incubated for 10 hours in an aqueous solution of protein A (Sigma Chemicals, 1 mg/ml). To neutralise any still free adsorption sites, the sensor is washed with distilled water and then incubated again for 1 hour in a solution of phosphate buffer which contains 10 g/l of bovine serum albumin (Sigma Chemicals).

The sample solution is continuously flowed for 9 minutes over the sensor surface on which protein A is adsorbed.

The isotropically emitted fluorescence, the evanescently back-coupled fluorescence and the transmission are measured over these 9 minutes in accordance with the description given in 1.1. A sensitivity of c. 1×10−10 M, based on F-IgG, is achieved.

In all the following Application Examples, the sensor platform desribed in Example 1 and the optical arrangement described therein is used.

EXAMPLE 2

Detection of Fluorescein-Labelled Immunoglobulin on Immobilised Protein A

Solutions Used:

1) buffer solution: consisting of 0.5 l of phosphate puffer (0.041 M of $Na_2HPO_4$+0.028 M of $KH_2PO_4$), 0.151 M of NaCl, 250 mg/l of sodium azide, 50 ml of methanol, 1 g/l of bovine serum albumin (BSA); 0.5 ml of POE-(20)-sorbitol monolaurate (Tween 20, ICI), bulked to 1 liter with distilled water;

2) solution for immobilising protein A (Sigma Chemicals): 1 mg/ml of dist. water;

3) neutralisation solution: buffer solution 1)+10 mg/ml of bovine serum albumin (BSA, Sigma Chemicals);

4) rinsing solution: buffer solution 1);

5) sample solutions: fluorescein-labelled immunoglobulin 10−8 M in buffer solution 1;

6) regeneration solution: glycine buffer, pH 2.

Process:

The optical sensor platform is incubated for 10 hours with solution 2) to immobilise protein A. To neutralise any still free adsorption sites, the sensor platform is washed with distilled water and then incubated again for 1 hour in the neutralisation solution which contains 10 g/l of BSA.

The process consists of the following individual steps which are carried out in a flow cell (flow rate 1 ml/min):

washing for 5 minutes with buffer solution 1), followed by recording of background signal;

addition of sample solution 5) over 9 minutes;

washing for 5 minutes with buffer solution 1);

addition for 5 minutes of regeneration solution 6);

washing for 5 minutes with buffer solution 1).

The isotropically emitted fluorescence and the fluorescence coupled back to the sensor platform as well as the transmission are measured during the entire process in accordance with Example 1.

In addition to a strong signal of the isotropically emitted fluorescence, strong signals from the back-coupled fluorescence as well as a markedly diminished transmission in the presence of the analyte are measured. The fluorescence signals increase during the addition of the fluorescent analyte and show the typical shape of an adsorption curve. The signal for the back-coupled fluorescence is, at the same enhancement, lower than the isotropically emitted fluorescence only by a factor of 2. The transmission signal has a shape that is virtually a mirror inversion of the fluorescence signals. Until the maximum fluorescence is attained, the transmission signal decreases by 25%. The transmission signal increases again by the same amount as the fluorescence decreases after the regeneration step.

EXAMPLE 3

Detection of Fluorescein-Labelled Immunoglobulin on Immobilised Protein A

Solutions used:

1) buffer solution: consisting of ⅓ of phosphate puffer (0.041 M of $Na_2HPO_4$+0.028 M of $KH_2PO_4$), 0.151 M of NaCl, 200 mg/l of sodium azide, 50 ml of methanol, bulked to 1 liter with distilled water;
2) solution for immobilising protein A (Sigma Chemicals): 1 mg/ml of buffer solution 1);
3) neutralisation solution: buffer solution 1)+10 mg/ml of bovine serum albumin (BSA, Sigma Chemicals)
4) rinsing solution: is also used for detecting the background signal, buffer solution 1+1 mg/ml of BSA;
5) sample solutions: fluorescein-labelled immunoglobulin M in different concentrations (10–8 M, 10–9 M, 10–10 M, 10–11 M) in buffer solution 1) with 1 mg/ml of BSA;
6) regeneration solution: glycine buffer, pH 2.5.

Process:

The optical sensor platform is incubated for 2 hours with the solution for immobilising protein A. To neutralise any still free adsorption sites, the sensor is washed with distilled water and then incubated again for 1 hour in a solution of phosphate buffer which contains 10 g/l of BSA.

The process consists of the following individual steps:

washing for 2 minutes with rinsing solution 4) (0.1 ml/min), recording the background signal;

simultaneous aspiration of the sample (1 ml) into a loop via an automatated sampler;

then passing the sample for c. 7 minutes over the sensor platform by discharging the loop (0.1 m/min, between start and end pulse);

afterwards rinsing with solution 4);

after application of the regeneration solution again rinsing with solution 4).

The isotropically emitted fluorescence and the transmission are measured during the entire process in accordance with Example 1.

A further distinct fluorescence signal is observed at a concentration of $10^{-10}$ M of fluorescein-labelled immunoglobulin A. Changes in the transmission are determined at concentrations of up to $10^{-8}$ M.

After averaging the data (9 point averages), an analyte concentration of $10^{-11}$ M can still be found.

At the different concentrations, the following changes of signal are recorded at the end of the addition of sample, compared with the initial background signal (signal/noise ratio between 1 and 4 mV):

| [F-IgG] | Fluorescence signal (V) | Change of the transmission signal |
|---|---|---|
| $10^{-8}$ M | 1.0 | –10% |
| $10^{-9}$ M | 0.2 | not determined |
| $10^{-10}$ M | 0.039 | not determined |
| $10^{-11}$ M (after averaging) | 0.008 | not determined |

The detection limit is below $10^{-11}$ M, corresponding to an analyte concentration of $10^{-14}$ mol of fluorescein-labelled IgG.

EXAMPLE 4

1.4. Detection of Fluorescein-Labelled Oligonucleotides with Immobilised Complementary Strands in a Hybridisation Assay Solutions used:

1) hybridisation buffer (pH 7.75), consisting of 0.069 M of phosphate buffer (0.041 M $NaH_2PO_4$+0.028 M $NaH_2PO_4$), 0.176 M of KCl, 1 ml of POE-(20) sorbitol monolaurate (Tween 20, ICI), 1 g of polyacrylic acid PAA 5100, 500 mg/l of sodium azide, bulked to 1 liter with distilled water;
2) sample solutions: fluorescein-labelled oligomer complementary to the oligomer immobilised on the sensor platform and consisting of 16 base pairs (fluorescein-5'-GTTGTGTGGAATTGTG-3' (10–12 M/l) in hybridisation buffer 1);
3) regeneration solution: 50% (G/G) of urea in aqueous solution.

Process:

The capture probe is synthesized with an oligonucleotide synthesizer (Applied Biosystems 394B) 3'CAACACACCTTAACAC-5' direct on a sensor platform silanised with 3-glycidyloxypropyltrimethoxysilane by a standard process as used for oligonucleotide synthesis on particles (e.g. in M. J. Gait, Oligonucleotide Synthesis. A practical approach. Oxford University Press, NY 1990). But unlike the standard synthesis, 4-(4,4-dimethoxytrityl) hydroxybutyric acid is used as stable linking group for anchoring on the surface at the 3'-end so as to prevent a later splitting off from the sensor surface. After washing with water, the sensor platforms are used with the immobilised detection strands in the detection method.

The method consists of the following individual steps:

washing for 8 minutes with hybridisation buffer 1) (0.5 ml/min), recording the background signal;

adding the sample solution 2) (0.05 ml/min) over 26 minutes (after 5 sec flush of 5 ml/min);

rinsing for 4 minutes with hybridisation buffer 1) (0.5 ml/min);

adding the regeneration solution 3) over 4 minutes (0.5 ml/min);

rinsing for 4 minutes with hybridisation buffer 1) (0.5 ml/min).

The isotropically emitted fluorescence and the transmission are measured during the process in accordance with Example 1. After addition of the sample over 10 minutes, corresponding to an amount of 500 attomol of fluorescein-labelled tracer DNA, a fluorescence signal of 20 mV is observed at a signal noise of c. 1 mV.

What is claimed is:

1. A process for detecting luminescence with a planar dielectric optical sensor platform comprising a transparent substrate (a) to which a thin transparent waveguiding layer (b) is applied, which sensor platform is provided with a grating for the input-coupling of the excitation light and the refractive index of said substrate (a) is lower than the refractive index of the waveguiding layer (b), by bringing a liquid sample into contact with the layer (b), and measuring the luminescence produced by substances having luminescence properties in the sample, or by substances having luminescence properties immobilised on the layer (b), optoelectronically, wherein (A) the excitation light is coupled into the planar waveguide and traverses the waveguiding layer, whereby the substances having luminescence properties are excited to luminescence in the evanescent field of the waveguiding layer, (B) the grating has a depth modulation of 3 to 60 nm, (C) the thickness of the layer (b) is 40 to 160 nm, and (D) the ratio of depth modulation to the thickness of the layer (b) is smaller than 0.5.

2. A process according to claim 1, wherein essentially parallel light is used for exciting luminescence.

3. A process according to claim 1, wherein laser light of wavelength 300 to 1100 nm is used for exciting luminescence.

4. A process according to claim 1, wherein laser light of wavelength 450 to 850 nm is used for exciting luminescence.

5. A process according to claim 1, wherein laser light of wavelength 480 to 700 nm is used for exciting luminescence.

6. A process according to claim 1, wherein the substances capable of luminescence used for detecting the analyte are immobilised direct on the surface of the waveguiding layer.

7. A process according to claim 1, which comprises immobilising a specific binding partner as chemical or biochemical detector substance for the analyte itself or for one of the binding partners on the surface of the sensor platform in a multi-step assay in the course of which the analyte becomes bound in one of the partial steps.

8. A process according to claim 1, which comprises detecting the isotropically emitted, evanescently excited luminescence.

9. A process according to claim 1, which comprises detecting at the edges of the sensor platform the evanescently excited luminescence coupled back into said sensor platform.

10. A process according to claim 1, which comprises detecting the isotropically emitted luminescence as well as the evanescently excited light which is coupled back, independently of each other but simultaneously.

11. A process according to claim 1, which comprises determining simultaneously the absorption of the excitation light coupled into the waveguide.

12. A process according to claim 1, wherein the excitation light is coupled into the waveguide in continuous wave (cw) mode.

13. A process according to claim 1, which comprises input-coupling the excitation light in the form of a timed pulse and detecting the luminescence time-resolved.

14. A process according to claim 13, wherein the pulse length is adjusted from one picosecond up to 100 seconds.

15. A process according to claim 1, which comprises input-coupling the excitation light with modulated intensity at one or more than one frequency, and detecting the resultant phase shift and modulation of the sample luminescence.

16. A process according to claim 1, wherein the sample to be detected is egg yolk, blood, serum, plasma or urine.

17. A process according to claim 1, wherein the sample to be detected is a surface water, a soil or plant extract, a bioprocess broth or synthesis broth.

18. A process according to claim 1, wherein a biochemical substance is quantitatively determined by the detection of luminescence.

19. A process according to claim 1, wherein antibodies or antigens are quantitatively determined by the detection of luminescence.

20. A process according to claim 1, wherein receptors, oligonucleotides, DNA strands, RNA strands, DNA analogs, RNA analogs, enzymes, enzyme substrates, enzyme cofactors, enzyme inhibitors, lectins or carbohydrates are quantitatively determined by the detection of luminescence.

21. A process according to claim 1, wherein in luminescent components present in optically turbid fluids are quantitatively determined by the detection of luminescence.

22. An optical sensor platform comprising a transparent substrate (a) to which a thin transparent waveguiding layer (b) is applied, which sensor platform is provided with a grating for the input-coupling of the excitation light and the refractive index of said substrate (a) is lower than the refractive index of the waveguiding layer (b), wherein (A) the grating has a depth modulation of 3 to 60 nm, (B) the thickness of the layer (b) is 40 to 160 nm, and (C) the ratio of depth modulation to the thickness of the layer (b) is smaller than 0.5.

23. An optical sensor platform according to claim 22, wherein the substrate comprises quartz, an inorganic glass or a plastics material.

24. An optical sensor platform according to claim 22, wherein the substrate comprises an inorganic glass.

25. An optical sensor platform according to claim 22, wherein the substrate comprises polycarbonate or polymethylmethacrylate.

26. An optical sensor platform according to claim 22, wherein an interlayer comprising $SiO_2$, a thermoplastic, thermosetting or structurally crosslinked plastic is provided between the substrate and the waveguiding layer, which interlayer has a refractive index lower than, or identical to, that of the substrate.

27. An optical sensor platform according to claim 22, wherein the interlayer has a thickness of, or less than, 10 $\mu$m.

28. An optical sensor platform according to claim 22, wherein the planar transparent waveguiding layer is a material having a refractive index greater than 2.

29. An optical sensor platform according to claim 22, wherein the planar transparent waveguiding layer comprises $Ta_2O_5$ or $TiO_2$.

30. An optical sensor platform according to claim 22, wherein the planar transparent waveguiding layer has a thickness of 80 nm to 160 nm.

31. An optical sensor platform according to claim 22, wherein the grating for the input-coupling of excitation light is an optical diffraction grating.

32. An optical sensor platform according to claim 31, wherein the optical diffraction grating is a relief grating.

33. An optical sensor platform according to claim 31, wherein the grating has the form of a sinusoidal, sawtooth or rectangular curve.

34. An optical sensor platform according to claim 31, wherein the grating has a grating period of 200 to 1000 nm.

35. An optical sensor platform according to claim 31, wherein the grating has a depth modulation of 5 to 30 nm.

36. An optical sensor platform according to claim 31, wherein the grating has a line to space ratio of 0.5 to 2.

37. An optical sensor platform according to claim 22, wherein an adhesion promoting layer is present between the waveguiding layer and the sample.

38. An optical sensor platform according to claim 37, wherein the adhesion promoting layer has a thickness of or less than 50 nm.

39. An optical sensor platform according to claim 22, wherein the sensor platform is regenerable and can be used repeatedly.

40. An optical sensor platform according to claim 22, wherein a substance having luminescence properties or a binding partner for an analyte is immobilised on the surface of the waveguding layer.

41. An apparatus for the detection of luminescence comprising a sensor platform according to claim 22, a coherent light source; and a detector unit for the measurment of evanescently exited luminescence.

* * * * *